(12) United States Patent
Coffey (10) Patent No.: US 7,763,252 B2
(45) Date of Patent: *Jul. 27, 2010

(54) METHODS FOR THE TREATMENT OF CELLULAR PROLIFERATIVE DISORDERS

(75) Inventor: Matthew C. Coffey, Calgary (CA)

(73) Assignee: Oncolytics Biotech Inc., Calgary, Alberta ( * ) Notice: Subject to any disclaimer, the term of this patent is extended or adjusted under 35 U.S.C. 154(b) by 388 days.

This patent is subject to a terminal disclaimer.

(21) Appl. No.: 11/807,908

(22) Filed: May 30, 2007

(65) Prior Publication Data

US 2008/0057073 A1 Mar. 6, 2008

Related U.S. Application Data

(60) Continuation of application No. 11/394,609, filed on Mar. 31, 2006, which is a division of application No. 09/985,756, filed on Nov. 6, 2001, now Pat. No. 7,052,832.

(60) Provisional application No. 60/246,728, filed on Nov. 9, 2000.

(51) Int. Cl.
*A61K 39/395* (2006.01)
*C12Q 1/02* (2006.01)
*A61P 43/00* (2006.01)

(52) U.S. Cl. ............... 424/159.1; 424/93.6; 435/15; 435/29; 436/64

(58) Field of Classification Search ............... None
See application file for complete search history.

(56) References Cited

U.S. PATENT DOCUMENTS 5,023,252 A 6/1991 Hseih

FOREIGN PATENT DOCUMENTS

WO WO 99/08692 2/1999
WO WO 00/50051 3/2000

OTHER PUBLICATIONS

Archer, S.G., et al. (1995). Expression of ras p21, p53 and c-erbB-2 in advanced breast cancer and response to first line hormonal therapy. Br J Cancer. 72(5):1259-1266.
Armstrong, G.D., et al. (1984). Studies on reovirus receptors of L cells: virus binding characteristics and comparison with reovirus receptors of erythrocytes. Virology. 138(1):37-48.
Barbacid, M. (1987). ras genes. Annu Rev Biochem. 56:779-827.
Baselga, J., et al. (1996). Phase II study of weekly intravenous recombinant humanized anti-p185HER2 monoclonal antibody in patients with HER2/neu-overexpressing metastatic breast cancer. J Clin Oncol. 14(3):737-744.
Bos, J.L., (1989). ras oncogenes in human cancer: a review. Cancer Res. 49(17):4682-4689.
Carter, P., et al. (1992). Humanization of an anti-p185HER2 anitbody for human cancer therapy. Proc Natl Acad Sci USA. 89(10):4285-4289.
Chandron, K., and Nibert, M.L. (1998). Protease cleavage of reovirus capsid protein μ1/μ1C is blocked by alkyl sulfate detergents, yielding a new type of infectious subvirion particle. J Virol. 72(1):467-475.
Chaubert, P., et al. (1994). K-ras mutations and p53 alterations in neoplastic and nonneoplastic lesions associated with longstanding ulcerative colitis. Am J Pathol. 114(4):767-775.
Clark, E.A., and Brugge, J.S. (1995). Integrins and signal transduction pathways: the road taken. Science. 268(5208):233-239.
Clark, J.W., et al. (1996). Effects of tyrosine kinase inhibitors on the proliferation of human breast cancer cell lines and proteins important in the ras signaling pathway. Int J Cancer. 65(2):186-191.
Coffey, M.C., et al. (1998). Reovirus therapy of tumors with activated Ras pathway. Science. 282(5392):1332-1334.
Cuff, C.F., et al. (1998). Enteric reovirus infection as a probe to sutdy immunotoxicity of the gastrointestinal tract. Toxicol Sci. 42(2):99-108.
Di Domenico M., et al. (1996). Estradiol activation of human colon carcinoma-derived Caco-2 cell growth. Cancer Res. 56(19):4516-4521.
Duncan, R., et al. (1991). Conformational and functional analysis of the C-terminal globular head of the reovirus cell attachment protein. Virology. 182(2):810-819.
Dvorak, H.F., et al. (1988). Identification and characterization of the blood vessels of solid tumors that are leaky to circulating macromolecules. Am J Pathol. 133(1):95-109.

(Continued)

*Primary Examiner*—Larry R. Helms
*Assistant Examiner*—Lei Yao
(74) *Attorney, Agent, or Firm*—Fish & Richardson P.C.

(57) ABSTRACT

The present invention relates to methods of identifying the susceptibility of cells to reovirus infection by measuring constitutive ras-MAP signaling. The invention also pertains to methods using reovirus for the treatment of cellular proliferative disorders, and particularly cellular proliferative disorders wherein the proliferating cells exhibit constitutive MAPK phosphorylation, in mammals. In particular, the methods provide for reovirus treatment of mammals to treat proliferative disorders which include breast tumors, a subset of tumors in which mutation of the ras gene is not believed to play a significant role.

14 Claims, 3 Drawing Sheets

OTHER PUBLICATIONS

Gentsch, J.R., and Pacitti, A.F. (1985). Effect of neuraminidase treatment of cells and effect of soluble glycoproteins on type 3 reovirus attachement to murine L cells. J Virol. 56(2):356-364.

Harwerth, I.M., et al. (1992). Monoclonal antibodies against the extracellular domain of the erbB-2 receptor function as partial ligand agonist. J Biol Chem. 267(21):15160-15167.

Hudziak, R.M., et al. (1989). p185HER2 monoclonal antibody has antiproliferative effects in vitro and sensitizes human breast tumor cells to tumor necrosis factor. Mol Cell Biol. 9(3):1165-1172.

Hung, M.C., et al. (1995). HER-2/neu-targeting gene therapy—a review. Gene. 159(1):65-71.

Ikeda, K., et al. (1999). Oncolytic virus therapy of multiple tumors in the brain requires suppression of innate and elicited antiviral responses. Nat Med. 5(8):881-887.

Ikeda, K., et al. (2000). Complement depletion facilitates the infection of multiple brain tumors by an intravascular, replication-conditional herpes simplex virus mutant. J Virol. 74(10):4765-4775.

Jacobs, C., and Rubsamen, H. (1983). Expression of pp60c-src protein kinase in adult and fetal human tissue: high activites in some sarcomas and mammary carcinomas. Cancer Res. 43(4):1696-1702.

Janes, P.W., et al. (1994). Activation of the Ras signalling pathway in human breast cancer cells overexpressing erbB-2. Oncogene. 9(12):3601-3608.

Jardines, L., et al. (1993). neu(c-erbB-2/HER2) and the epidermal growth factor receptor (EGFR) in breast cancer. Pathobiology. 61(5-6):268-282.

Koenders, P.G., et al. (1991). Epidermal growth factor receptor-negative tumors are predominantly confined to the subgroup of estradiol receptor-positive human primary breast cancers. Cancer Res. 51(17):4544-4548.

Lee, J.M., and Bernstein, A. (1993). p53 mutations increase resistance to ionizing radiation. Proc Natl Acad Sci USA. 90(12):5742-5746.

Lee, P.W., et al. (1981). Characterization of anti-reovirus immunoglobulins secreted by cloned hybridoma cell lines. Virology. 108(1):134-146.

Levitzki, A. (1994). Signal-transduction therapy. A novel approach to disease management. Eur J Biochem. 226(1):1-13.

Lowe, S.W., et al. (1994). p53 status and the efficacy of cancer therapy in vivo. Science. 266(5186):807-810.

Mah, D.C., et al. (1990). The N-terminal quarter of reovirus cell attachment protein σ1 possesses intrinsic virion-anchoring function. Virology. 179(1):95-103.

Migliaccio, A., et al. (1996). Tyrosine kinase/p21ras/MAP-kinase pathway activation by estradiol-receptor complex in MCF-7 cells. EMBO J. 15(6):1292-1300.

Migliaccio, A., et al. (1998). Activation of the Src/p21ras/Erk pathway by progesterone receptor via cross-talk with estrogen receptor. EMBO J. 17(7):2008-2018.

Mills, N.E., et al. (1995). Increased prevalence of K-ras oncogene mutations in lung adenocarcinoma. Cancer Res. 55(7):1444-1447.

Nagy, J.A., et al. (1989). Pathogenesis of tumor stroma generation: a critical role for leaky blood vessels and fibrin deposition. Biochim Biophys Acta. 948(3):305-326.

Nguyen, D.H., et al. (1999). Myosin light chain kinase functions downstream of Ras/ERK to promote migration of urokinase-type plasminogen activator-stimulated cells in an integrin-selective manner. J Cell Biol. 146(1):149-164.

Norman, K.L., and Lee, P.W. (2000). Reovirus as a novel oncolytic agent. J Clin Invest. 105(8):1035-1038.

Paasinen-Sohns, A., and Hölttä, E. (1997). Cells transformed by ODC, c-Ha-ras and v-src exhibit MAP kinase/Erk-independent constitutive phosphorylation of Sos, Raf and c-Jun activation domain, and reduced PDGF receptor expression. Oncogene. 15(16):1953-1966.

Paul, R.W., et al. (1989). The α-anomeric form of sialic acid is the minimal receptor determinant recognized by reovirus. Virology. 172(1):382-385.

Pietras, R.J., et al. (1994). Antibody to HER-2/neu receptor blocks DNA repair after cisplatin in human breast and ovarian cancer cells. Oncogene. 9(7):1829-1838.

Raybaud-Diogene, H., et al. (1997). Markers of radioresistance in squamous cell carcinomas of the head and neck: a clinicopathologic and immunohistochemical study. J Clin Oncol. 15(3):1030-1038.

Robinson, M.J., and Cobb, M.H. (1997). Mitogen-activated protein kinase pathways. Curr Opin Cell Biol. 9(2):180-186.

Rosen, L. (1960). Serologic grouping of reoviruses by hemagglutination-inhibition. Am J Hyg. 71:242-249.

Shackney, S.E., et al. (1998). Intracellular coexpression of epidermal growth factor receptor, Her-2/neu, and p21ras in human breast cancers: evidence for the existence of distinctive patterns of genetic evolution that are common to tumors from different patients. Clin Cancer Res. 4(4):913-928.

Slamon, D.J., et al. (1989). Studies of the HER-2/neu proto-oncogene in human breast and ovarian cancer. Science. 244(4905):707-712.

Smith, R.E., et al. (1969). Polypeptide components of virions, top component and cores of reovirus type 3. Virology. 39(4):791-810.

Spandidos, D.A. (1987). Oncogene activation in malignant transformation: a study of H-ras in human breast cancer. Anticancer Res. 7(5B):991-996.

Stanley, N.F. (1967). Reoviruses. Br Med Bull. 23(2):150-154.

Strong, J.E., et al. (1993). Evidence that the epidermal growth factor receptor on host cells confers reovirus infection efficiency. Virology. 197(1):405-411.

Strong, J.E., and Lee, P.W. (1996). The v-erbB oncogene confers enhanced cellular susceptibility to reovirus infection. J Virol. 70(1):612-616.

Strong, J.E., et al. (1998). The molecular basis of viral oncolysis: usurpation of the Ras signaling pathway by reovirus. EMBO J. 17(12):3351-3362.

Thirukkumaran, C.M., et al. (2001). Reovirus induces apoptosis in breast and prostate cell lines and activates Nf-κβ in the nucleus: implications for a prognostic factor in successful reovirus therapy. Proceedings of the American Association for Cancer Research. 42:455 (abstract).

Turner, D.L., et al. (1992). Site-directed mutagenesis of the C-terminal portion of reovirus protein σ1: evidence for a conformation-dependent receptor binding domain. Virology. 186(1):219-227.

Tyler, K.L., et al. (1999). Molecular basis of viral apoptosis: reovirus-induced apoptosis is associated with activation of nuclear transcription factor Nf-κβ via the MAP kinases MEKK1 and NIK. Neurology. 52(6):A186 (abstract).

Verbeek, B.S., et al. (1996). c-Src protein expression is increased in human breast cancer. An immunohistochemical and biochemical analysis. J pathol. 180(4):383-388.

von Lintig, F.C., et al. (2000). Ras activation in human breast cancer. Breast Cancer Res Treat. 62(1):51-62.

Wiesmuller, L., and Wittinghofer, F. (1994). Signal transduction pathways involving Ras. Mini review. Cell Signal. 6(3):247-267.

Wilsbacher, J.L., et al. (1999). Phosphorylation of MAP kinases by MAP/ERK involves multiple regions of MAP kinases. J Biol Chem. 274(24):16988-16994.

Yip-Schneider, M.T., et al. (1999). Lack of elevated MAP kinase (Erk) activity in pancreatic carcinomas despite oncogenic K-ras expression. Int J Oncol. 15(2):271-279.

Zhou, D.J., et al. (1989). Proto-oncogene abnormalities in human breast cancer: c-ERBB-2 amplification does not correlate with recurrence of disease. Oncogene. 4(1):105-108.

Current Protocols in Molecular Biology, Detection of MAP Kinase Signaling, Unit 14.3, print publication date: Oct. 1998.

FIGURE 1

A Immunoprecipitation

B Phospho-MAPK

C Total MAPK

METHODS FOR THE TREATMENT OF CELLULAR PROLIFERATIVE DISORDERS

RELATED APPLICATIONS

This application is a continuation of U.S. application Ser. No. 11/394,609, filed Mar. 31, 2006, which is a divisional of U.S. application Ser. No. 09/985,756, filed Nov. 6, 2001, now U.S. Pat. No. 7,052,832, issued May 30, 2006, which claims the benefit of U.S. Provisional Application Ser. No. 60/246, 728, filed Nov. 9, 2000, the contents of which are incorporated herein by reference.

FIELD OF THE INVENTION

The present invention relates to methods of identifying the susceptibility of cells to reovirus infection by measuring constitutive ras-MAP signaling. The invention also pertains to methods using reovirus for the treatment of cellular proliferative disorders, and particularly cellular proliferative disorders wherein the proliferating cells exhibit constitutive MAPK phosphorylation, in mammals. In particular, the methods provide for reovirus treatment of mammals to treat proliferative disorders which include breast tumors, a subset of tumors in which mutation of the ras gene is not believed to play a significant role.

REFERENCES

The following publications, patent applications and patents are cited in this application:

U.S. Pat. No. 5,023,252.
WO 99/08692, published Feb. 25, 1999.
Archer et al. (1995), *Br. J. Cancer* 72:1259-1266.
Armstrong, G. D. et al. (1984), *Virology* 138:37.
Barbacid, M., *Annu. Rev. Biochem.*, 56:779-827 (1987).
Baselga et al. (1996), *J. Clin. Onc.* 14:737-744.
Bos, J. (1989) *Cancer Res.* 49:4682.
Carter et al. (1992), *PNAS* 89:4285-4289.
Chandron and Nibert, "Protease cleavage of reovirus capsid protein mu1 and mu1C is blocked by alkyl sulfate detergents, yielding a new type of infectious subvirion particle", *J. of Virology* 72(1):467-75 (1998).
Chaubert, P. et al. (1994), *Am. J. Path.* 144:767.
Clark et al. (1995), *Science* 268:233-239.
Clark et al. (1996), *Intl. J. Cancer* 65:186-191.
Cuff et al., "Enteric reovirus infection as a probe to study immunotoxicity of the gastrointestinal tract" *Toxicological Sciences* 42(2):99-108 (1998)
DiDomenico et al. (1996), *Cancer Res.* 56:4516-4521
Duncan et al., "Conformational and functional analysis of the C-terminal globular head of the reovirus cell attachment protein" *Virology* 182(2):810-9 (1991).
Dvorak et al. (1988), *Am J Path* 133:95-109.
Fields, B. N. et al. (1996), Fundamental Virology, 3rd Edition, Lippincott-Raven.
Gentsch, J. R. K. and Pacitti, A. F. (1985), *J. Virol.* 56:356.
E. Harlow and D. Lane, "Antibodies: A laboratory manual", Cold Spring Harbor Laboratory (1988).
Harweth et al. (1992), *J Biol Chem* 267:15160-15167.
Hudziak et al. (1989), *Mol Cell Biol* 9:1165-1172.
Hung et al. (1995), *Gene* 159:65-71.
Jacobs et al. (1983), *Cancer Res* 43:1696-1702.
Janes, P. W., et al. (1994) *Oncogene* 9:3601.
Jardines et al. (1993) *Pathobiology* 61:268-282.
Koenders et al. (1991), *Cancer Res* 51:4544-4548.
Lee. J. M. et al. (1993) *PNAS* 90:5742-5746.
Lee, P. W. K. et al. (1981)*Virology*, 108:134-146.
Levitzki, A. (1994) *Eur. J. Biochem.* 226:1.
Lowe. S. W. et al. (1994) *Science*, 266:807-810.
Mah et al., "The N-terminal quarter of reovirus cell attachment protein sigma 1 possesses intrinsic virion-anchoring function" *Virology* 179(1):95-103 (1990).
Migliaccio et al. (1996), *EMBO J.* 15:1292-1300.
Migliaccio et al. (1998), *EMBO J.* 17:2008-2018.
Millis, N E et al. (1995) *Cancer Res.* 55:1444.
Nagy et al. (1989) *Biochim Biophys Acta* 948:305-326.
Paul R. W. et al. (1989) *Virology* 172:382-385.
Pietras et al. (1994), *Oncogene* 9:1829-1838.
Raybaud-Diogene. H. et al. (1997) *J. Clin. Oncology*, 15(3): 1030-1038.
Remington's Pharmaceutical Sciences, Mace Publishing Company, Philadelphia Pa. 17$^{th}$ ed. (1985).
Rosen, L. (1960) *Am. J. Hyg.* 71:242.
Sabin, A. B. (1959), *Science* 130:966.
Shackney et al. (1998), *Clin Cancer Res* 4:913-928.
Slamon et al. (1989), *Science* 244:707-712.
Smith, R. E. et al., (1969) *Virology*, 39:791-800.
Spandiodos (1987), *Anticancer Res* 7:991-996.
Stanley, N. F. (1967) *Br. Med. Bull.* 23:150.
Strong, J. E. et al., (1993) *Virology*, 197:405-411.
Strong, J. E. and Lee, P. W. K., (1996) *J. Virol.*, 70:612-616.
Strong, J. E. et al., (1998) *EMBO J*, 17:3351-3362.
Turner and Duncan, "Site directed mutagenesis of the C-terminal portion of reovirus protein sigma1:evidence for a conformation-dependent receptor binding domain" *Virology* 186(1):219-27 (1992).
Verbeek et al. (1996) *J Path* 180:383-388.
Wiessmuller, L. and Wittinghofer, F. (1994), *Cellular Signaling* 6(3):247-267.
Zhou et al. (1989), *Oncogene* 4:105-108.

All of the above publications, patent applications and patents are herein incorporated by reference in their entirety to the same extent as if each individual publication, patent application or patent was specifically and individually indicated to be incorporated by reference in its entirety.

STATE OF THE ART

Normal cell proliferation is regulated by a balance between growth-promoting proto-oncogenes and growth-constraining tumor-suppressor genes. Tumorigenesis can be caused by genetic alterations to the genome that result in the mutation of those cellular elements that govern the interpretation of cellular signals, such as potentiation of proto-oncogene activity or inactivation of tumor suppression. It is believed that the interpretation of these signals ultimately influences the growth and differentiation of a cell, and that misinterpretation of these signals can result in neoplastic growth (neoplasia).

Genetic alteration of the proto-oncogene Ras is believed to contribute to approximately 30% of all human tumors (Wiessmuller, L. and Wittinghofer, F. (1994), *Cellular Signaling* 6(3):247-267; Barbacid, M. (1987) A *Rev. Biochem.* 56, 779-827). The role that Ras plays in the pathogenesis of human tumors is specific to the type of tumor. Activating mutations in Ras itself are found in most types of human malignancies, and are highly represented in pancreatic cancer (80%), sporadic colorectal carcinomas (40-50%), human lung adenocarcinomas (15-24%), thyroid tumors (50%) and myeloid leukemia (30%) (Millis, N E et al. (1995) *Cancer Res.* 55:1444; Chaubert, P. et al. (1994), *Am. J. Path.* 144:767; Bos, J. (1989) *Cancer Res.* 49:4682). Ras activation is also demonstrated by upstream mitogenic signaling elements, notably by tyrosine receptor kinases (RTKs). These upstream elements, if amplified or overexpressed, ultimately result in elevated Ras activity by the signal transduction activity of Ras. Examples of this include overexpression of PDGFR in certain forms of glioblastomas, as well as in c-erbB-2/neu in breast cancer (Levitzki, A. (1994) *Eur. J. Biochem.* 226:1; Janes, P. W., et al. (1994) *Oncogene* 9:3601; Bos, J. (1989) *Cancer Res.* 49:4682).

Current methods of treatment for neoplasia include surgery, chemotherapy and radiation. Surgery is typically used as the primary treatment for early stages of cancer; however, many tumors cannot be completely removed by surgical means. In addition, metastatic growth of neoplasms may prevent complete cure of cancer by surgery. Chemotherapy involves administration of compounds having antitumor activity, such as alkylating agents, antimetabolites, and anti-tumor antibiotics. The efficacy of chemotherapy is often limited by severe side effects, including nausea and vomiting, bone marrow depression, renal damage, and central nervous system depression. Radiation therapy relies on the greater ability of normal cells, in contrast with neoplastic cells, to repair themselves after treatment with radiation. Radiotherapy carrot be used to treat many neoplasms, however, because of the sensitivity of tissue surrounding the tumor. In addition, certain tumors have demonstrated resistance to radiotherapy and such may be dependent on oncogene or anti-oncogene status of the cell (Lee. J. M. et al. (1993) *PNAS* 90:5742-5746; Lowe. S. W. et al. (1994) *Science,* 266:807-810; Raybaud-Diogene. H. et al. (1997) *J. Clin. Oncology,* 15(3):1030-1038).

Breast cancer is amongst the most common and feared cancer in women with an estimated one in eight American women developing it in their lifetime (NCI-SEER, 1998). Although there have been tremendous achievements in breast cancer treatment that have allowed a stable mortality rate in the face of an increasing incident rate, most of these advances can be attributed to improved early detection methods and not novel treatment strategies. The fact that there have been few advances in the actual treatment of this affliction demands that the development of unconventional treatment strategies be explored.

Never in the history of cancer biology has there been a more promising period in the development of therapeutics for the treatment of breast cancer. Many of these therapeutics are targeted at specific receptors that are overexpressed in subsets of this cancer, and are now finding some clinical use. Perhaps one of the most promising of these new therapies is the use of antibodies targeted to the HER2 receptor that is frequently overexpressed in breast cancer. Results from the use of these monoclonal antibodies directed at the extracellular moieties of this growth factor receptor are promising, and indeed have met with some clinical success (Baselga, 1996; for reviews see Nass, 1998; Hung, 1995). There are however a number of technical obstacles that must be addressed. Firstly, these monoclonal antibodies directed against HER2 are not themselves cytocidal. but are rather cytostatic (Pietras, 1994; Harwerth, 1992; Hudziak, 1989; Carter, 1992). Importantly, in a SCID or nude mouse model, anti-HER2 antibodies are effective only in repressing tumor growth and not actually causing tumor regression. Further, this repression of tumor growth is alleviated rapidly once the antibody administration is ceased. On a more positive note, there is evidence that treatment of tumors with anti-HER2 antibodies in an immune competent animal may actually result in a cytocidal effect mediated by antibody-dependent cellular cytotoxicity (ADCC) (Carter, 1992). Secondly, targeting growth factor receptor (EGFR) may be of limited value, as not all breast cancers express these receptors at elevated levels. Additionally, this strategy targets only receptor tyrosine kinases and would have little therapeutic benefit for those breast cancers that overexpress non-receptor tyrosine kinases such as Src, which have already been implicated in the growth of some breast cancers (Clark, 1996). Finally, the biology of the tumor blood vessels must also be taken into account as far as the capacities to deliver these large macromolecules to their target cells. It has been demonstrated that the vasculature of a tumor is heterogeneous and the ability of a vessel to leak large macromolecules, such as antibodies, is a function of their spatial orientation to the tumor mass (Dvorak, 1988; Nagy and Dvorak, 1989). It has been shown that the vessels with the greatest permeability to these molecules reside primarily at the tumor-host interface, and the least permeable vessels are those that actually penetrate the tumour mass (Dvorak, 1988). The result of this differential permeability is that these tumour specific antibodies, and their cytocidal effector cells, would fail to penetrate into the tumour mass and would be only effective on the periphery of the mass.

Despite the fact that activating mutations in ras are infrequent in breast cancer, there is a growing body of evidence that activation of the Ras/MAPK pathway is important in the initiation and progression of this disease. Upstream elements of the Ras pathway, notably receptor tyrosine kinases (RTK) are frequently overexpressed in breast cancers. HER-2/neu (erbB-2) is overexpressed in approximately 30% of all breast cancers (Spandidos 1987; Zhou, 1989; Archer, 1995) and is associated with poor patient prognosis (Slamon, 1989). When overexpressed in NIH-3T3 cells, HER-2 mediates transformation; however, there does appear to be a threshold level of overexpression that is required for this transformation to occur (Jardines, 1993; Clark 1995). It appears that this transforming ability of HER-2 is dependent upon Ras activity as cell lines overexpressing HER-2 exhibit a dramatic increase in MAP kinase activity, the latter being reflective of Ras activity (Janes, 1994). The growth factor receptor EGFR that is closely related to, but distinct from HER-2, has also been observed to be overexpressed in breast tumors and has also been correlated strongly with a poor patient prognosis (Shackney, 1998: Koenders, 1991).

Additional elements upstream of Ras have also been implicated in the etiology of breast cancer. The non-receptor tyrosine kinase c-Src has been implicated as being as important candidate in promoting the progression of breast cancer. A number of studies indicate a –4 to –30 fold increase of c-Src activity in primary breast cancer tumors when compared to normal breast tissue (Verbeeks, 1996; Jacobs and Rubsamen, 1983). C-Src has been suggested to also play an important role in the transmission of signals from both the estrogen and progestin receptors via the Ras/MAPK pathway. A number of groups have observed that the treatment of breast tumor derived MCF-7 cells with estradiol results in the activation of c-Src kinase activity with resultant activation of MAPK (Di Domenico, 1996; Migliaccio, 1996). More recently, Migliaccio (1998), has demonstrated in T47D breast cancer cells that progestin stimulated cell proliferation is dependent upon Src/Ras/MAPK signaling. The fact that these steroid receptors can utilize Ras for their signaling suggests that Ras may play a more pivotal role in the promotion of growth in ER and PR positive breast tumors.

Ras itself may also play a more pivotal role in the development of breast cancer that was initially thought. Although activating mutations in Ras are rare in breast cancer development, overexpression of normal H-Ras has been observed in breast tumors (Shackney, 1998; Spandidos, 1987). This overexpression of Ras may provide an additional mechanism of uncoupling normal signal transduction and promote a tumorigenic state. Taken together these observations suggest the feasibility of targeting an activated Ras pathway in the development of novel breast cancer therapeutics.

Previously we have demonstrated that reovirus is replication competent in only those cells that contained an activated Ras signaling pathway, either through direct mutation of Ras itself or via upstream elements that result in its activation (Strong, 1993; Strong, 1998). Additionally, we were able to demonstrate that reovirus could act against tumors containing a Ras activation in vivo (Coffey, 1998). Using the human glioblastoma cell line U87, we established a tumor xenograft SCID mouse model. U87 cells were selected as an appropriate model as they overexpress the RTK PDGF that results in Ras activation and demonstrate acute susceptibility to reovirus infection in vitro. SCID mice were implanted with a U87 tumor xenograft and following palpable tumor establishment the tumors were treated with a single intratumor injection of reovirus. This single treatment resulted in dramatic tumor regression.

In view of the drawbacks associated with the current means for treating neoplastic growth, the need still exists for improved methods for the treatment of most types of cancers and, particularly, breast cancer. It would be useful to have a means available to determine reovirus susceptibility to predict the effectiveness of reovirus treatment.

SUMMARY OF THE INVENTION

The present invention is directed to methods of identifying the susceptibility of cells to reovirus infection by measuring constitutive ras-MAP signaling. The invention also provides methods using reovirus for the treatment of cellular proliferative disorders, and particularly cellular proliferative disorders wherein the proliferating cells exhibit constitutive MAPK phosphorylation, in mammals. In particular, the methods provide for reovirus treatment of mammals to treat proliferative disorders which include breast tumors, a subset of tumors in which mutation of the ras gene is not believed to play a significant role.

This invention also pertains to methods for preventing reovirus recognition in the treatment of cellular proliferative disorders, and particularly cellular proliferative disorders which exhibit constitutive MAPK phosphorylation, in mammals. The mammal may be selected from dogs, cats, sheep, goats, cattle, horses, pigs, mice, humans and non-human primates. The method comprises administering to the proliferating cells an effective amount of one or more reoviruses under conditions which result in substantial lysis of the proliferating cells.

The reovirus may be a mammalian reovirus or an avian reovirus. The reovirus may be modified such that the outer capsid is removed, the virion is packaged in a liposome or micelle or the proteins of the outer capsid have been mutated. The reovirus agent can be administered in a single dose or in multiple doses. The proliferative disorder may be a neoplasm. Both solid and hematopoietic neoplasms can be targeted. Use of preceding, concurrent or subsequent immunosuppression may result in more effective reovirus treatment.

Accordingly, in one aspect the invention provides a method of determining cellular susceptibility to reovirus infection by measuring constitutive ras-MAP signaling, wherein the presence of said signaling indicates susceptibility to infection by reovirus. Constitutive ras-MAP signaling results in activation of the MAP kinase whether there is a mitogen or not, and activation of the MAP kinase leads to phosphorylation of MAP kinase. Therefore, the state of MAP kinase phosphorylation can be determined as a measure of constitutive ras-MAP signaling. The state of MAP kinase phosphorylation can be determined by any method established in the art, and in particular by using an antibody specific for phosphorylated MAP kinase.

Accordingly, the present invention can be used to diagnose proliferative disorders which can be treated with reovirus. Thus, a biological sample can be collected from a mammal suspected of having a proliferative disorder and cells in the sample are tested for constitutive ras-MAP signaling according to the present invention. The proliferative disorder may be any condition associated with abnormally active cell growth, such as neurofibromatosis. More preferably, the proliferative disorder is selected from the group consisting of lung cancer, prostate cancer, colorectal cancer, thyroid cancer, renal cancer, adrenal cancer, liver cancer, pancreatic cancer, breast cancer and central and peripheral nervous system cancer. A particularly preferred proliferative disorder is breast cancer.

The present invention is applicable to any animal with a proliferative disorder. Preferably, the animal is a mammal. More preferably, the animal is selected from the group consisting of dogs, cats, sheep, goats, cattle, horses, pigs, mice, non-human primates, and humans. Most preferably, the animal is human.

In a further aspect, the invention provides a method of treating a proliferative disorder in a mammal, which disorder is characterized by proliferating cells which exhibit constitutive MAPK phosphorylation, comprising administering to the proliferating cells in said mammal an effective amount of one or more reoviruses under conditions which result in substantial lysis of the proliferating cells. Methods which further comprise a step selected from the group consisting of: administering to the proliferating cells in said mammal an effective amount of an immune suppressive agent; removing B-cells or T-cells from said mammal; removing anti-reovirus antibodies from said mammal; removing antibodies from said mammal; administering anti-antireovirus antibodies to said mammal; and suppressing the immune system of the mammal are also provided, as are methods which further comprise administration of a chemotherapeutic agent.

Also provided is a method of treating a neoplasm in a human, which neoplasm is characterized by proliferating cells which exhibit constitutive MAPK phosphorylation, comprising administering to the neoplasm a reovirus in an amount sufficient to result in substantial oncolysis of the neoplastic cells. Preferably, the reovirus is administered systemically or by injection into or near a solid neoplasm. Methods further comprising the step of previously, concurrently or subsequently suppressing or otherwise compromising the immune system of the mammal are also included.

Also provided is a method of inhibiting metastasis of a neoplasm in a mammal, which neoplasm is characterized by proliferating cells which exhibit constitutive MAPK phosphorylation, comprising administering to the mammal a reovirus in an amount sufficient to result in substantial lysis of the neoplastic cells. Methods further comprising the step of previously, concurrently or subsequently suppressing or otherwise compromising the immune system of the mammal are also included.

Also provided is a method of treating a suspected neoplasm in a mammal, which neoplasm is characterized by proliferating cells which exhibit constitutive MAPK phosphorylation, comprising surgical removal of substantially all of the neoplasm and administration of an effective amount of reovirus at or near to the surgical site resulting in oncolysis of any remaining neoplastic cells. The reovirus may also be administered systemically. Methods further comprising the step of previously, concurrently or subsequently suppressing or otherwise compromising the immune system of the mammal are also included.

Also provided is a pharmaceutical composition comprising an effective amount of a reovirus and a pharmaceutically acceptable excipient. Also provided is a pharmaceutical composition comprising an immunosuppressant or is immunoinhibitant, a reovirus and a pharmaceutically acceptable excipient. Kits comprising a reovirus and, optionally, an immunosuppressant or immunoinhibitant are also provided.

The methods and pharmaceutical compositions of the invention provide an effective means to treat neoplasia, without the side effects associated with other forms of cancer therapy. When used, inhibition or suppression of the immune system increases the availability of reovirus to infect and lyse proliferating cells which exhibit constitutive MAPK phosphorylation because anti-reovirus antibodies are not formed. Because reovirus is not known to be associated with disease, any safety concerns associated with deliberate administration of a virus are minimized.

The foregoing and other objects, features and advantages of the invention will be apparent from the following more particular description of preferred embodiments of the invention, as illustrated in the accompanying drawings.

BRIEF DESCRIPTION OF THE DRAWINGS

FIG. 1 shows the effect of v-src transformation on host cell susceptibility to reovirus infection. Uninfectable NIH-3T3 parental cells and v-src transformed NIH-3T3 cells were grown to 80% confluency in a 24 well plate and were then exposed to reovirus at an estimated MOI of 80 PFU per cell. Cells and media were harvested at the indicated times post infection and resultant lysate was used for plaque titration assay. V-src transformed NIH-3T3 cells (closed circles), NIH-3T3 parentals (open circles). (Mean±standard deviation).

FIGS. 2A to 2C illustrate in vitro rovirus replication in human breast tumor cell lines. (A) Reovirus protein synthesis in mock-infected and reovirus-infected breast cancer cell lines. Cells were labeled with [$^{35}$S]-methionine from 46 to 48 hours after infection. Lysates were prepared and subsequently immunoprecipitated with a polyclonal anti-reovirus type 3 serum and then analyzed by SDS-PAGE. Reovirus proteins are indicated on the right. (B) Reovirus infectivity correlates with constitutive MAPK phosphorylation. The breast tissue cell line HBL-100 and the breast tumor cell lines MDA-MB-468, MCF7, MDA-MB-435, T47D and SK-BR-3 were plated in a six well plate. Cells were either grown in the presence of 10% FCS or were serum starved (0.5% FCS) for a 48 hour period. Monolayers were washed in PBS and cell lysates were prepared and subjected to SDS-PAGE. Following blotting onto nitrocellulose paper, samples were probed with antibodies directed against phospho-MAPK Phospho-MAPK levels were all standardized by total MAPK levels. (C) Total MAPK levels in the human breast tissue and breast cancer cell lines.

DETAILED DESCRIPTION OF THE INVENTION

Previously we have shown that the human reovirus could be used as an effective oncolytic agent against human glioblastoma xenografts in a SCID mouse model (WO 99/08692). Here we have found that cellular susceptibility to reovirus infection may be determined by measuring constitutive ras-MAP signaling of the cell, since the presence of such signaling indicates susceptibility to infection by reovirus. We also present evidence that reovirus is useful as an oncolytic agent against mammary tumors. Although ras mutations are infrequent in the etiology of breast cancer, aberrant Ras/MAPK signaling via upstream signal elements, such as receptor tyrosine kinases and non-receptor tyrosine kinases (such as c-Src), is common.

For the same reasons that the treatment of breast cancers with monoclonal antibodies may be impaired (see discussion above), reovirus may be an attractive cancer therapy. Firstly, reovirus itself is a cytocidal agent and does not rely upon immune effector cells to cause tumor regression. Indeed, the natural mechanism of killing infected cells is via direct lysis due to viral replication (Tyler and Fields, 1996). Secondly, it targets those breast cancers in which there is activation of Ras. This activation is not restricted to activating mutations of Ras (admittedly a rare subset of breast tumors) but also includes activation of Ras caused by elements upstream of Ras itself. These elements include not only receptor tyrosine kinases such as EGFR and HER2, but also include non-receptor tyrosine kinases such as the Src family members. Taken together, this type of therapy could be used with great efficacy against a tumor type as heterogeneous as breast cancer and would not be as restricted a strategy as one that targets only on receptor. Finally, the inability of antibodies to penetrate into solid tumor masses suggests that reovirus, if delivered intratumorally, should replicate unheeded. Thus, it is useful to know whether the cells of a proliferative disorder are susceptible to infection by reovirus in order to predict the efficacy of such treatment.

To assess whether Src family kinases could mediate reovirus infection, uninfectable NIH-3T3 cells were transformed with v-src and were then challenged with reovirus. We determined that v-src signaling confers infectability to reovirus infection.

We next examined five breast cancer cell lines; MDA-MB-468, MCF7, MDA-MB-435, T47D, and SK-BR-3 as well as a cell line derived from normal breast tissue, HBL-100 for in vitro reovirus replication. All five of the tumor derived cell lines were infectable by reovirus while the HBL-100 was unable to effectively replicate the virus.

To determine if the Ras pathway was indeed activated in these cell lines, the level of MAPK phosphorylation was assessed in the presence and absence of serum. Those cell lines that were infectable exhibited constitutive MAPK phosphorylation even in the absence of mitogen, while the cell line which was not susceptible to reovirus infection displayed MAPK phosphorylation only in the presence of serum. Therefore, constitutive MAPK phosphorylation is an indication of susceptibility to reovirus infection.

To determine if reovirus could be used as an oncolytic agent in vivo against breast tumors, SCID mice were implanted with MDA-MB-468 human tumour xenographs. Following the establishment of palpable tumours, the mice were treated with a single injection of reovirus and tumour size was monitored for a four-week period. The single injection resulted in dramatic regression of the tumour size. Finally, the ability of reovirus to act against primary breast cancer tumours was determined, and the results indicate that reovirus was capable of replicating in biopsy samples collected from various patients. Therefore, many breast tumors are susceptible to reovirus infection.

The name reovirus (Respiratory and enteric orphan virus) is a descriptive acronym suggesting that these viruses, although not associated with any known disease state in humans, can be isolated from both the respiratory and enteric tracts (Sabin, A. B. (1959), *Science* 130:966). The term "reovirus" refers to all viruses classified in the reovirus genus.

Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (Sabin, A. B. (1959), *Science* 130: 966; Fields, B. N. et al. (1996), *Fundamental Virology, 3rd Edition*, Lippincott-Raven; Rosen, L. (1960) *Am. J. Hyg.* 71:242; Stanley, N. F. (1967) *Br. Med. Bull.* 23:150).

Although reovirus is not known to be associated with any particular disease, many people have been exposed to reovirus by the time they reach adulthood (i.e., fewer than 25% in children <5 years old, to greater than 50% in those 20-30 years old (Jackson G. G. and Muldoon R. L. (1973) *J. Infect. Dis.* 128:811; Stanley N. F. (1974) *In: Comparative Diagnosis of Viral Diseases*, edited by E. Kurstak and K. Kurstak, 385-421, Academic Press, New York).

For mammalian reoviruses, the cell surface recognition signal is sialic acid (Armstrong, G. D. et al. (1984), *Virology* 138:37; Gentsch, J. R. K. and Pacitti, A. F. (1985), *J. Virol.* 56:356; Paul R. W. et al. (1989) *Virology* 172:382-385) Due to the ubiquitous nature of sialic acid, reovirus binds efficiently to a multitude of cell lines and as such can potentially target many different tissues; however, there are significant differences in susceptibility to reovirus infection between cell lines.

As described herein, Applicant have discovered that cells which exhibit constitutive MAPK phosphorylation are susceptible to reovirus infection. "Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription: while viral transcripts were produced, virus proteins were not expressed.

The implantation of human tumor cells into SCID mice is recognized as a well known model system for testing the effectiveness of various anti-tumor agents in humans. It has previously been shown that pharmaceuticals effective against human tumors implanted into SCID mice are predictive of their effectiveness against the same tumors in humans.

Based upon these discoveries, Applicant have developed methods for determining susceptibility to reovirus infection by measuring constitutive ras-MAP signaling and methods for treating proliferative disorders in mammals wherein the proliferating cells exhibit constitutive MAPK phosphorylation. Representative mammals include dogs, cats, sheep, goats, cattle, horses, pigs, mice, non-human primates, and humans. In a preferred embodiment, the mammal is a human.

In the diagnostic methods of the invention, the level of MAPK phosphorylation of proliferating cells is determined in the presence or absence of mitogen. The presence of such constitutive ras-MAP signaling in the cells is indicative of susceptibility to reovirus infection.

In the treatment methods of the invention, reovirus is administered to proliferating cells in the individual mammal exhibiting constitutive MAPK phosphorylation. In one embodiment of this invention a course of reovirus therapy is administered one or more times.

In the methods of the invention, reovirus is administered to proliferating cells in the individual mammal exhibiting constitutive MAPK phosphorylation. Representative types of human reovirus that can be used include type 1 (e.g., strain Lang or T1L); type 2 (e.g., strain Jones or T2J); and type 3 (e.g., strain Dearing or strain Abney, T3D or T3A); other strains of reovirus can also be used.

In a preferred embodiment, the reovirus is human reovirus serotype 3, more preferably the reovirus is human reovirus serotype 3, strain Dearing. Alternatively, the reovirus can be a non-human mammalian reovirus (e.g., non-human primate reovirus, such as baboon reovirus; equine; or canine reovirus), or a non-mammalian reovirus (e.g., avian reovirus). A combination of different serotypes and/or different strains of reovirus, such as reovirus from different species of animal, can be used.

The reovirus may be naturally occurring or modified. The reovirus is "naturally-occurring": when it can be isolated from a source in nature and has not been intentionally modified by humans in the laboratory. For example, the reovirus can be from a "field source": for example, from a patient.

The reovirus may be modified but still capable of lytically infecting a mammalian cell exhibiting constitutive MAPK phosphorylation. The reovirus may be chemically or biochemically pretreated (e.g., by treatment with a protease, such as chymotrypsin or trypsin) prior to administration to the proliferating cells.

Pretreatment with a protease removes the outer coat or capsid of the virus and may increase the infectivity of the virus. The reovirus may be coated in a liposome or micelle (Chandron and Nibert, "Protease cleavage of reovirus capsid protein mu1 and mu1C is blocked by alkyl sulfate detergents, yielding a new type of infectious subvirion particle", *J. of Virology* 72(1):467-75 (1998)) to reduce or prevent an immune response from a mammal which has developed immunity to the reovirus. For example, the virion may be treated with chymotrypsin in the presence of micelle forming concentrations of alkyl sulfate detergents to generate a new infectious subviral particle (ISVP). An ISVP may be used either alone or in combination with whole virus to provide an agent that is either poorly recognized or has not been previously prevented by the patient's immune system.

The reovirus may be a recombinant reovirus from two or more types of reoviruses with differing pathogenic phenotypes such that it contains different antigenic determinants thereby reducing or preventing an immune response by a mammal previously exposed to a reovirus subtype. Such recombinant virions, also known as reassortants, can be generated by co-infection of mammalian cells with different subtypes of reovirus with the resulting resorting and incorporation of different subtype coat proteins into the resulting virion capsids.

The reovirus may be modified by incorporation of mutated coat proteins, such as for example σ1, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS1 cells will result in the incorporation of the mutated protein into the reovirus virion particle (Turner and Duncan, "Site directed mutagenesis of the C-terminal portion of reovirus protein sigma1: evidence for a conformation-dependent receptor binding domain" *Virology* 186(1):219-27 (1992); Duncan et al., "Conformational and functional analysis of the C-terminal globular head of the reovirus cell attachment protein" *Virology* 182(2):810-9 (1991); Mah et al., "The N-terminal quarter of reovirus cell attachment protein sigma 1 possesses intrinsic virion-anchoring function" *Virology* 179 (1):95-103 (1990))

The reovirus is preferably a reovirus modified to reduce or eliminate an immune reaction to the reovirus. Such modified reovirus are termed "immunoprotected reovirus". Such modifications could include packaging of the reovirus in a liposome, a micelle or other vehicle to mask the reovirus from the mammals immune system. Alternatively, the outer capsid of the reovirus virion particle may be removed since the proteins present in the outer capsid are the major determinant of the host humoral and cellular responses.

A "proliferative disorder" is any cellular disorder in which the cells proliferate more rapidly than normal tissue growth. Thus a "proliferating cell" is a cell that is proliferating more rapidly than normal cells. The proliferative disorder, includes but is not limited to neoplasms. A neoplasm is an abnormal tissue growth, generally forming a distinct mass, that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. A tumor is the neoplastic growth of the disease cancer. As used herein, a "neoplasm", also referred to as a "tumor", is intended to encompass hematopoietic neoplasms as well as solid neoplasms. Other proliferative disorders include, but are not limited to neurofibromatosis.

At least some of the cells of the proliferative disorder which are treated using the methods of the present invention exhibit constitutive MAPK phosphorylation. Similarly, at least some of the cells which are determined to be susceptible to reovirus infection using the methods of the present invention exhibit constitutive MAPK phosphorylation.

"B-cells" refers to B-lymphocytes. There are two major subpopulations of B lymphocytes, B-1 and B-2 cells. B-1 cells are self-renewing and frequently secrete high levels of antibody which binds to a range of antigens (polyspecificity) with a relatively low affinity. The majority of B cells, B-2 cells, are directly generated from precursors in the bone marrow and secrete highly specific antibody.

"T-cells" refers to T-lymphocytes. T-cells differentiate within the thymus gland and are specialized to operate against cells bearing intracellular organisms. T-cells only recognize antigen when it is on the surface of a body cell.

"Anti-reovirus antibody" refers to an antibody which binds to reovirus. "IgG antibodies" refers to immunoglobulin G antibodies. IgG, the most abundant type of antibody, carries the major burden of neutralizing bacterial toxins and binding to microorganisms to enhance their phagocytosis. "Humanized antibodies" refers to antibody molecules in which the amino acid sequence in the non-antigen binding regions has been altered so that the antibody more closely resembles a human antibody, and still retains its original binding ability.

"Administration to a proliferating cell or neoplasm" indicates that the reovirus is administered in a manner so that it contacts the proliferating cells or cells of the neoplasm (also referred to herein as "neoplastic cells"). The route by which the reovirus is administered, as well as the formulation, carrier or vehicle, will depend on the location as well as the type of the neoplasm. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases or brain tumors, the reovirus is administered in a manner such that it can be transported systemically through the body of the mammal and thereby reach the neoplasm (e.g., intrathecally, intravenously or intramuscularly). Alternatively, the reovirus can be administered directly to a single solid neoplasm, where it then is carried systemically through the body to metastases. The reovirus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

Reovirus can be administered systemically to mammals which are immune compromised or which have not developed immunity to the reovirus epitopes. In such cases, reovirus administered systemically, i.e. by intraveneous injection, will contact the proliferating cells resulting in lysis of the cells. Where the mammals to be treated have higher titers of anti-reovirus antibodies, more reovirus must be administered to be effective.

Immunocompetent mammals previously exposed to a reovirus subtype may have developed humoral and/or cellular immunity to that reovirus subtype. Nevertheless, it has been found that direct injection of the reovirus into a solid tumor in immunocompetent mammals will result in the lysis of the neoplastic cells. On the other hand, when the reovirus is administered systemically to immunocompetent mammals, the mammals may produce an immune response to the reovirus. Such an immune response may be avoided if the reovirus is of a subtype to which the mammal has not developed immunity, or the reovirus has been modified as previously described herein such that it is immunoprotected, for example, by protease digestion of the outer capsid or packaging in a micelle.

Alternatively, it is contemplated that the immunocompetency of the mammal against the reovirus may be suppressed either by the prior or co-administration of pharmaceuticals known in the art to suppress the immune system in general (Cuff et al., "Enteric reovirus infection as a probe to study immunotoxicity of the gastrointestinal tract" *Toxicological*

*Sciences* 42(2):99-108 (1998)) or alternatively the administration of such immunoinhibitors as anti-antireovirus antibodies. The humoral immunity of the mammal against reovirus may also be temporarily reduced or suppressed by plasmaphoresis of the mammals blood to remove the anti-reovirus antibodies. The humoral immunity of the mammal against reovirus may additionally be temporarily reduced or suppressed by the intraveneous administration of non-specific immunoglobulin to the mammal.

It is contemplated that the reovirus may be administered to immunocompetent mammals immunized against the reovirus in conjunction with the administration of immunosuppressants and/or immunoinhibitors. Such immunosuppressants and immunoinhibitors are known to those of skill in the art and include such agents as cyclosporin, rapamycin, tacrolimus, mycophenolic acid, azathioprine and their analogs, and the like. Other agents are known to have immunosuppressant properties as well (see, e.g., Goodman and Gilman, $7^{th}$ Edition, page 1242, the disclosure of which is incorporated herein by reference). Such immunoinhibitors also include "anti-antireovirus antibodies," which are antibodies directed against anti-reovirus antibodies. Such antibodies can be made by methods known in the art. See for example "Antibodies: A laboratory manual" E. Harlow and D. Lane, Cold Spring Harbor Laboratory (1988). Such anti-antireovirus antibodies may be administered prior to, at the same time or shortly after the administration of the reovirus. Preferably an effective amount of the anti-antireovirus antibodies are administered in sufficient time to reduce or eliminate an immune response by the mammal to the administered reovirus. The terms "immunosuppressant" or "immune suppressive agent" include conventional immunosuppressants, immunoinhibitors, antibodies, and conditions such as radiation therapy or HIV infection which result in compromise of the immune system.

The term "substantial lysis" means at least 10% of the proliferating cells are lysed, more preferably of at least 50% and most preferably of at least 75% of the cells are lysed. The percentage of lysis can be determined for tumor cells by measuring the reduction in the size of the tumor in the mammal or the lysis of the tumor cells in vitro.

A "mammal suspected of having a proliferative disorder" means that the mammal may have a proliferative disorder or tumor or has been diagnosed with a proliferative disorder or tumor or has been previously diagnosed with a proliferative disorder or tumor, the tumor or substantially all of the tumor has been surgically removed and the mammal is suspected of harboring some residual tumor cells.

This invention also includes pharmaceutical compositions which contain, as the active ingredient, one or more immunosuppressants or immunoinhibitors and one or more of the reoviruses associated with "pharmaceutically acceptable carriers or excipients". In making the compositions of this invention, the active ingredients/immunosuppressant or immunoinhibitor and reovirus are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredients/immunosuppressant or immunoinhibitor and reovirus are mixed with a pharmaceutical excipient to form a solid preformulation composition containing homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*, the disclosure of which is incorporated herein by reference.

The immunosuppressant or immunoinhibitor and reovirus or the pharmaceutical composition comprising the immunosuppressant or immunoinhibitor and reovirus may be packaged into convenient kits providing the necessary materials packaged into suitable containers. It is contemplated the kits may also include chemotherapeutic agent.

The immunosuppressant or immunoinhibitor is administered in an appropriate amount and using an appropriate schedule of administration sufficient to result in immunosuppression or immunoinhibition of the mammal's immune system. Such amounts and schedules are well known to those of skill in the art.

The reovirus is administered in an amount that is sufficient to treat the proliferative disorder (e.g., an "effective amount"). A proliferative disorder is "treated" when administration of reovirus to the proliferating cells effects lysis of the proliferating cells. This may result in a reduction in size of the neoplasm, or in a complete elimination of the neoplasm. The reduction in size of the neoplasm, or elimination of the neoplasm, is generally caused by lysis of neoplastic cells ("oncolysis") by the reovirus. Preferably the effective amount is that amount able to inhibit tumor cell growth. Preferably the effective amount is from about 1.0 pfu/kg body weight to about $10^{15}$ pfu/kg body weight, more preferably from about $10^2$ pfu/kg body weight to about $10^{13}$ pfu/kg body weight. For example, for treatment of a human, approximately $10^2$ to $10^{17}$ plaque forming units (PFU) of reovirus can be used, depending on the type, size and number of tumors present. The effective amount will be determined on an individual basis and may be based, at least in part, on consideration of the type of reovirus; the chosen route of administration; the individual's size, age, gender; the severity of the patient's symptoms; the size and other characteristics of the neoplasm; and the like. The course of therapy may last from several days to several months or until diminution of the disease is achieved.

The immunosuppressant or immunoinhibitor and reovirus can be administered in a single dose, or multiple doses (i.e., more than one dose). The multiple doses can be administered concurrently, or consecutively (e.g., over a period of days or weeks). The reovirus can also be administered to more than one neoplasm in the same individual.

The compositions are preferably formulated in a unit dosage form, each dosage containing an appropriate amount of immunosuppressant or immunoinhibitor and from about $10^2$ pfus to about $10^{13}$ pfus of the reovirus. The term "unit dosage forms" refers to physically discrete units suitable as unitary dosages for human subjects and other mammals, each unit containing a predetermined quantity of reovirus calculated to produce the desired therapeutic effect, in association with a suitable pharmaceutical excipient.

As mentioned above, it has been found that the reovirus is effective for the treatment of solid neoplasms in immunocompetent mammals. Administration of unmodified reovirus directly to the neoplasm results in oncolysis of the neoplastic cells and reduction in the size of the tumor in immunocompetent animals. When animals are rendered immunosuppressed or immunodeficient in some way, systemic administration of reovirus will be more effective in producing oncolysis.

It is contemplated that the reovirus may be administered in conjunction with surgery or removal of the neoplasm. Therefore, provided herewith are methods for the treatment of a solid neoplasm comprising surgical removal of the neoplasm and administration of a reovirus at or near to the site of the neoplasm.

It is contemplated that the reovirus may be administered in conjunction with or in addition to radiation therapy which renders the mammal immunosuppressed.

It is further contemplated that the reovirus of the present invention may be administered in conjunction with or in addition to known anticancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etopside, pregnasome, platinum compounds such as carboplatin and cisplatin, taxanes such as taxol and taxotere, hormone therapies such as tamoxifen and anti-estrogens, interferons, aromatase inhibitors, progestational agents and LHRH analogs.

The reovirus and immunosuppressants of the present invention have been found to reduce the growth of tumors that are metastatic. In an embodiment of the invention, a method is provided for reducing the growth of metastatic tumors in a mammal comprising administering an effective amount of a reovirus to the immunosuppressed mammal.

Utility

The diagnostic methods of the present invention may be used to identify the susceptibility of cells to reovirus infection by measuring constitutive ras-MAP signaling. This will be useful to determine in what cases reovirus treatment of cellular proliferative disorders is likely to be effective.

The reoviruses and immunosuppressants of the present invention may be used for a variety of purposes. They may be used in methods for treating proliferative disorders which exhibit constitutive MAPK phosphorylation in a mammal. They may be used to reduce or eliminate neoplasms. They may be used in methods for treating metastases. They may be used in conjunction with known treatments for cancer including surgery, chemotherapy and radiation.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

μM=micromolar
mM=millimolar
M=molar
ml=milliliter
μl=microliter
mg=milligram
μg=microgram
PAGE=polyacrylamide gel electrophoresis
rpm=revolutions per minute
FBS=fetal bovine serum
DTT=dithiothrietol
SDS=sodium dodecyl sulfate
PBS=phosphate buffered saline
DMEM=Dulbecco's modified Eagle's medium
α-MEM=α-modified Eagle's medium β-ME=β-mercaptoethanol
MOI=multiplicity of infection
PFU=plaque forming units
MAPK=MAP kinase
phosph-MAPK=phosphorylated-MAP kinase
HRP=horseradish-peroxidase
PKR=double-stranded RNA activated protein kinase
RT-PCR=reverse transcriptase-polymerase chain reaction
GAPDH=glyceraldehyde-3-phosphate dehydrogenase
EGFR=epidermal growth factor receptors
MEK kinase=mitogen-activated extracellular signal-regulated kinase
DMSO=dimethylsulfoxide
SCID=severe combined immunodeficiency General Methods Cells and Virus Parental NIH-3T3 cells along with NIH-3T3 cells transformed with v-Src were a generous gift of Dr. Jove (University of Florida). Breast tumor cell lines MDA-MB-468, MCF7, MDA-MB-435, T-47D, SK-BR-3 and the control HBL-100 cells, were a generous gift of Dr. Karl Riabowol (University of Calgary). All cell lines were grown in Dulbecco's modified Eagle's medium (DMEM) containing 10% fetal bovine serum (FBS).

The Dearing strain of reovirus serotype 3 used in these studies was propagated in suspension cultures of L cells and purified according to Smith et al (1969) with the exception that β-mercaptoethanol (β-ME) was omitted from the extraction buffer.

Infection of Cells and Quantitation of Virus

Confluent monolayers of cells were grown in 24-well plates and infected with reovirus at an estimated multiplicity of infection of 80 PFU/cell. After 1 hr incubation at 37° C., the monolayers were washed with warm DMEM-10% FBS, and then incubated in the same medium. At various times postinfection, a mixture of NP-40 and sodium deoxycholate was added directly to the medium on the infected monolayers to final concentrations of 1% and 0.5% respectively. The lysates were then harvested and virus yields were determined by plaque titration on L-929 cells.

Radiolabelling of Reovirus-Infected Cells and Preparation of Lysates

Subconfluent monolayers (80% confluent) of cells were infected with reovirus (MOI-10 PFU/cell). At 46 hours after infection, the media was replaced with methionine-free DMEM containing 10% FBS and 0.1 mCi/ml [$^{35}$S]-methionine. After further incubation for 2 hours at 37° C., the cells were washed in phosphate-buffered saline (PBS) and lysed in the same buffer containing 1% Triton X-100, and 0.5% sodium deoxycholate. Lysates were then boiled and stored at −70° C. until use.

Immunoprecipitation and SDS-PAGE Analysis

Immunoprecipitation of $^{35}$S-labeled reovirus-infected cell lysates with anti-reovirus serotype 3 serum was carried out as previously described (Lee, P. W. K. et al. (1981) *Virology*, 108:134-146).

Detection of Phospho-MAPK and Total MAPK

The 'PhosphoPlus' p44/42 MAP kinase (Thr202/Tyr204) antibody kit (New England Biolabs) was used for the detection of MAP kinase in cell lysates according to the manufacturer's instructions. Briefly, subconfluent monolayer cultures were lysed with the recommended SDS-containing sample buffer, and subjected to SDS-PAGE, followed by electroblotting onto nitrocellulose paper. The membrane was then probed with the primary antibody (anti-total MAPK or anti-phospho-MAPK), followed by the horseradish peroxidase (HRP)-conjugated secondary antibody as described in the manufacturer's manual.

Severe Combined Immune Deficient (SCID) Mice

Five to eight week old male SCID mice were purchased from Charles River Canada and were treated according to a protocol approved by the University of Calgary Animal Care Committee.

Implantation of Allografts and Xenografts

Actively growing MDA-MB-468 human breast cancer cells were harvested, washed, and resuspended in sterile PBS at a density of $2\times10^7$ cells/ml. $2.0\times10^6$ cells in 100 μl were injected subcutaneously at a site overlying the hind flank. Implanted tumors were allowed to grow for 2-3 weeks until palpable tumors of 0.5×0.5 cm were obtained.

Intratumoral Injection of Reovirus

Once the established tumors obtained a treatable size, a single intratumoral injection of $1.0\times10^7$ PFUs of either live or UV-inactivated reovirus (serotype 3, strain Dearing) in 20 μl sterile PBS. Tumor size was measured twice weekly for a period of two to four weeks. Animals were sacrificed when they displayed severe morbidity due to excessive tumor burden or any observable level of distress.

Histoimmunological Analysis of Reovirus Infection

Immunofluorescent analysis was carried out using formalin-fixed, paraffin embedded tumor sections mounted on cover slips. After removal of paraffin by xylene, the sections were rehydrated, and exposed to the primary antibody (rabbit polyclonal anti-reovirus type 3 serum diluted 1/100 in PBS) for 2 h at room temperature. Following three washes with PBS, the sections were exposed to the secondary antibody [goat anti-rabbit IgG (whole molecule)-fluorescein isothiocyanate conjugate (FITC) or depending on the experiment, the same concentration of Cy3, diluted 1/100 in PBS containing 10% goat serum and 0.005% Evan's Blue counterstain] for 1 h at room temperature. As an additional counterstain, the nuclear stain DAPI, was also used. Finally, the fixed and treated sections were washed three more times with PBS and then once with double-distilled water. Slides were then dried and mounted on slides in 90% glycerol containing 0.1% phenylenediamine, and viewed with a Zeiss Axiophot microscope on which a Carl Zeiss camera was mounted (the magnification for all pictures was 200×).

Reovirus Infection of Primary Breast Tumor Samples

Biopsy breast tumor samples were sterilized by immersion in 95% ethanol followed by several washes of sterile PBS. The sample was then sliced into small sections and placed in a 24 well plate containing DMEM with 10% FCS. Reovirus was added ($1\times10^8$ PFUs). At various times post infection, samples were washed in sterile PBS and then fixed in formalin. Samples were then embedded in paraffin and sectioned for use in immunohistochemical analysis using antibodies directed against total reovirus proteins.

Example 1

Figure 1:
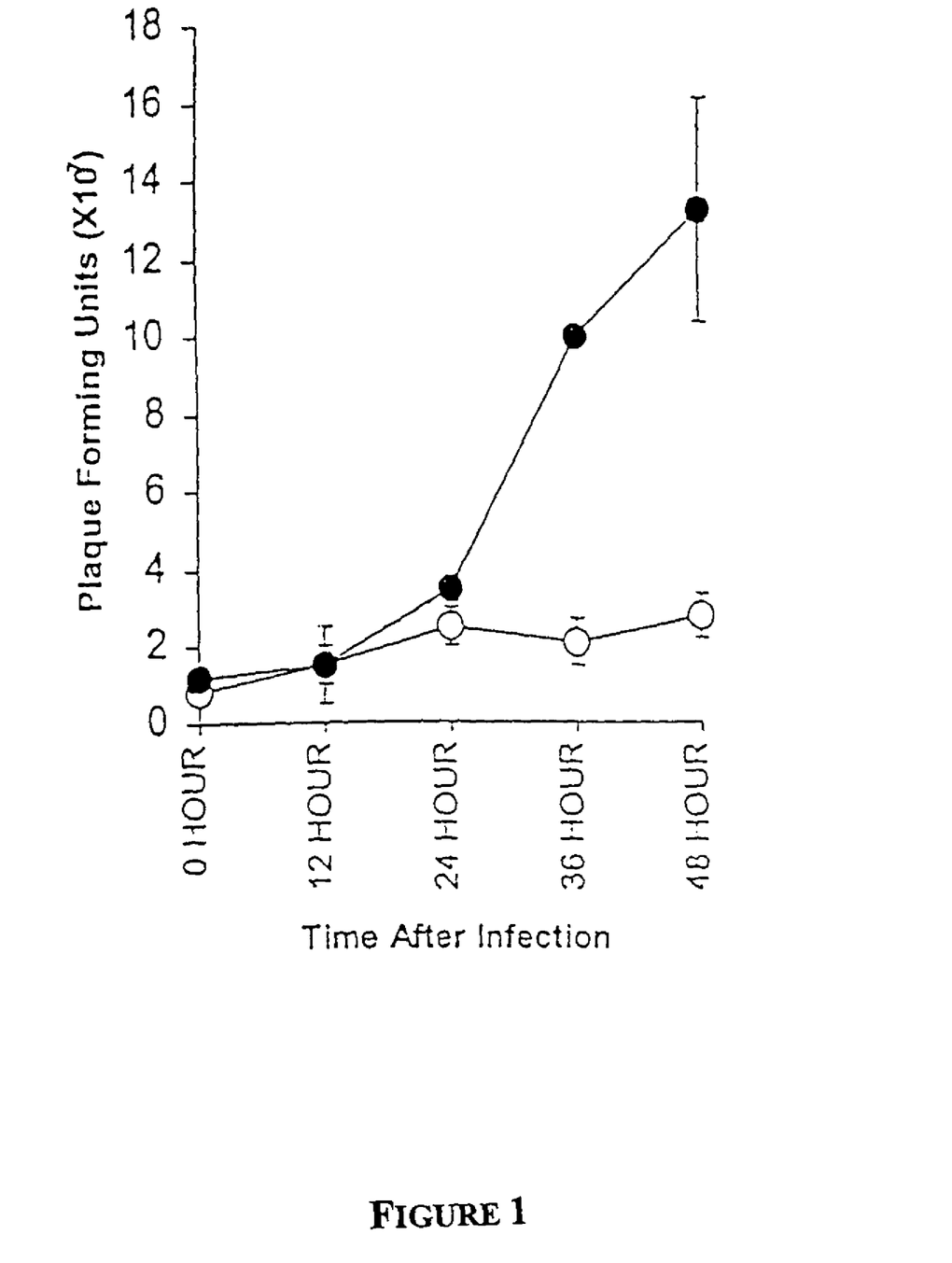

Transformation by the v-src Non-receptor Tyrosine Kinase Family Member Confers Susceptibility to Reovirus Infection Although we have previously demonstrated that transfection of uninfectable NR6 and NIH-3T3 cells with receptor tyrosine kinases was sufficient to allow reovirus replication (Strong, 1993), whether transfection of non-receptor tyrosine kinases could result in reovirus susceptibility was unknown. To determine whether activation of Src family kinases, which frequently contribute to the uncontrolled proliferation of many breast cancers, results in sufficient Ras activity to enable reovirus replication, uninfectable NIH-3T3 cells were transformed with v-src and susceptibility to reovirus was assessed. Confluent monolayers of v-src transformed NIH-3T3 or their parental cells were exposed to reovirus at a multiplicity of infection (MOI) of ~50 plaque forming units (PFUs) of reovirus. Cells and media were harvested at various times after infection and resultant samples were used for plaque titration analysis to determine reovirus replication. Our results show dramatic cytopathic effect in the v-src transformed cells by 48 hours postinfection (data not shown) as well as an enhanced reovirus output as measured by plaque titration assay. These results (FIG. 1) show that even non-receptor tyrosine kinases could potentially mediate reovirus infection and thus may be able to target an additional subset of breast tumors.

Example 2

Reovirus Can Infect a Panel of Human Breast Cancer Derived Cell Lines in which Constitutive Ras/MAPK Signaling can be Assessed To assess the feasibility of using reovirus against breast derived tumors a panel of breast cancer cells including: MDA-MB-468, MCF7, MDA-MB-435, T-47D, and SK-BR-3 was selected and susceptibility to reovirus infection in vitro was determined. As a control, HBL-100 cells, which are derived from normal breast tissue were used. These six cell lines were grown to 80% confluency and were then challenged with reovirus at an MOI of 10. Cells were labeled with [$^{35}$S] methionine for a two-hour period at 48 hours postinfection. Cells were then washed in phosphate-buffered saline and were lysed. The prepared lysates were then used for immunoprecipitation using antibodies directed against total reovirus protein. Immunoprecipitated proteins were analyzed by sodium dodecyl sulfate polyacrylamide gel electrophoresis (SDS-PAGE). The results (FIG. 2A) clearly demonstrate effective reovirus replication within the cell lines derived from breast tumor, however reovirus replication was restricted in the HBL-100 cell line. This suggests that these breast tumor cells are infectable as a result of an activation of Ras, either through a direct mutation or via an upstream signaling element. It is significant in that it suggests that a high percentage of breast cancers could potentially be treatable by therapeutics that target Ras, although this specific activation is rare in this cancer type.

Figure 2:
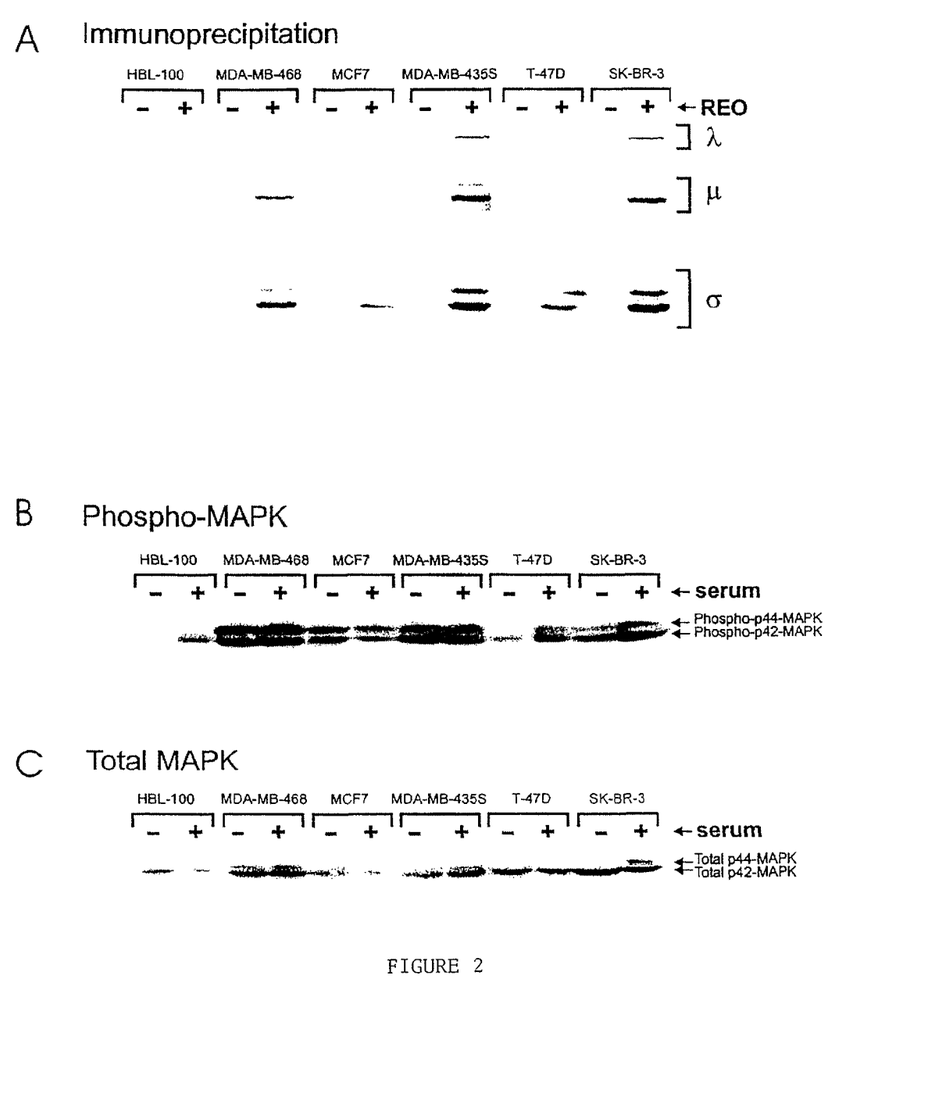

As MAPK phosphorylation is the inevitable result of signaling through Ras, the phosphorylated state of the protein should only be observed in a cell line with normal Ras signaling if a mitogenic stimulus is present. In a cell line with normal Ras signaling, the removal of these mitogenic stimuli should result in the cessation of signal through this pathway with a resultant dephosphorylation of MAPK. In a cell with aberrant Ras activity, either directly through mutational activation of Ras or alternatively via an upstream element, the phosphorylated form of MAPK should persist in either the presence or the absence of serum. To establish that the observed infectability in the breast tumor cell lines is a result of the activation of the Ras/MAPK signaling pathway, Western blot analysis of these cell lines was conducted using antibodies directed against phospho-MAPK. MDA-MB-468, MCF7, MDA-MB-435, T-47D, SK-BR-3 and HBL-100 cells were plated in a six well plate. Cells were then grown in 10% fetal calf serum (FCS) or were serum starved (0.5% FCS) for 48 hours. Cells were then washed in phosphate buffered saline (PBS) and were harvested in protein sample buffer. Cell lysates were subjected to SDS-PAGE and were subsequently blotted onto nitrocellulose paper and probed with anti-phospho-MAPK antibodies as recommended by the manufacturer. The results (FIG. 2B) clearly demonstrate that the only uninfectable cell line, HBL-100, possesses phospho-MAPK in the presence of serum and not in its absence, indicating that Ras signalling in this pathway is not aberrant. The remaining infectable cell lines have phospho-MAPK independent of the presence of mitogenic signals, as would be expected if they had constitutive activation of this pathway. Protein concentrations were standardized using antibodies directed against total MAPK (FIG. 2C).

Example 3

Reovirus can Act as an Anti-tumor Agent Against Breast Tumors In Vivo

Figure 3:
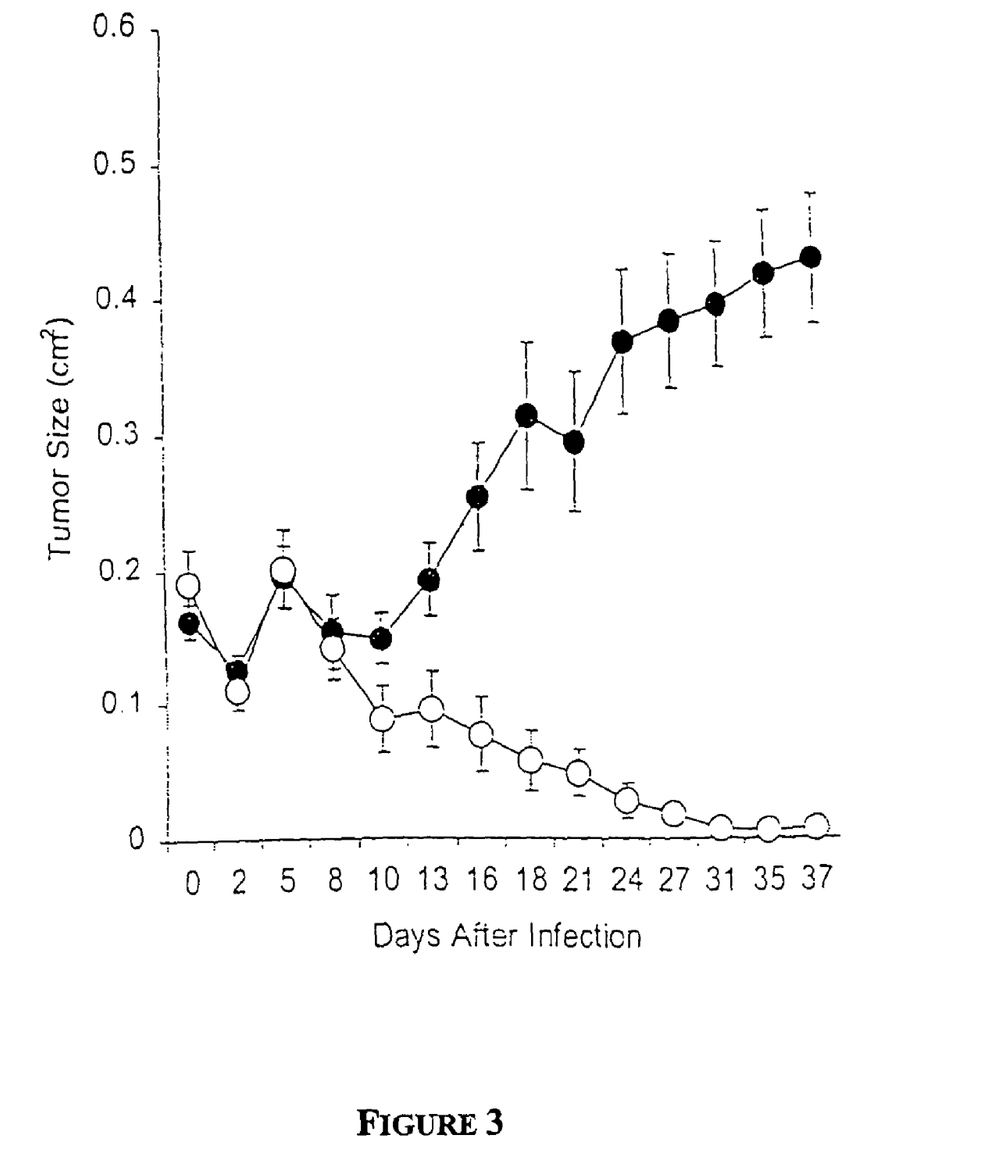
FIG. 3 illustrates reovirus-mediated in vivo oncolysis against human breast tumor xenograft. SCID mice were implanted subcutaneously and unilaterally with MDA-MB-468 human breast tumor xenografts. Following the establishment of a palpable tumor mass, a single intratumoral injection of either live reovirus (open circles) or UV-inactivated virus (closed circles) was administered and tumor growth was followed for a period of four weeks. (Mean±SEM).

The human breast cancer cell line, MDA-MB-468 was introduced as tumor xenografts subcutaneously into a site overlying the hind flank of SCID mice. Following palpable tumor establishment, the MDA-MB-468 tumor was administered a single intratumoral injection of $1.0\times10^7$ plaque forming units (PFUs) of reovirus serotype 3 (strain Dearing) in PBS. Control animals were given an intratumoral injection of UV-inactivated reovirus. Tumor growth was followed for a period of four weeks. As in demonstrated (FIG. 3), the reovirus treatment results in a dramatic regression in tumor size. As before, hematoxylin/eosin (HE) staining of the remaining mass indicated that the single reovirus injection results in the complete destruction of the tumor cells as compared to control tumors (data not shown). To determine if the observed lysis of the tumor cells was due to viral replication and to determine if there was spread of reovirus proteins beyond the tumor mass, immunofluorescence microscopy was conducted. Using antibodies directed against total reovirus proteins and paraffin embedded thin sections of the remaining tumor mass it was determined that reovirus replication is restricted to the MDA-MB-468 tumor cells and does not extend into the surrounding skeletal muscle.

Example 4

Reovirus can Replicate in Primary Breast Specimens

To ensure that the oncolytic effect of reovirus is not due to an innate characteristic of a passaged cell line, primary samples of human breast cancers were obtained to assess for reovirus infectability. Biopsy breast tumor samples were sterilized by immersion in 95% ethanol followed by several washes of sterile PBS. The sample was then sliced into small sections and placed in a 24 well plate containing DMEM with 10% FCS. Reovirus was added ($1\times10^8$ PFUs). At various times post infection, samples were washed in sterile PBS and then fixed in formalin. Samples were then embedded in paraffin and sectioned for use in immunohistochemical analysis using antibodies directed against total reovirus proteins. The results (not shown) clearly showed reovirus staining in those tumors challenged, demonstrating viral replication in these primary samples.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating a proliferative disorder in a subject, the method comprising:
   (a) diagnosing the proliferative disorder in the subject by:
      (i) identifying the subject as having a proliferative disorder;
      (ii) obtaining a sample from the subject comprising one or more cells of the proliferative disorder; and
      (iii) evaluating ras-MAP signaling in the cells, wherein constitutive ras-MAP signaling indicates that the subject has a proliferative disorder that can be treated with a reovirus; and
   (b) if the mammal has a proliferative disorder that can be treated with a reovirus, administering to the mammal an effective amount of one or more reoviruses under conditions that result in substantial lysis of cells of the proliferative disorder.

2. The method of claim 1, wherein the reovirus is selected from the group consisting of a mammalian reovirus and an avian reovirus.

3. The method of claim 1, wherein the reovirus is a mammalian reovirus.

4. The method of claim 1, wherein the reovirus is a human reovirus

5. The method of claim 1, wherein more than one type of reovirus is administered.

6. The method of claim 1, wherein more than one strain of reovirus is administered.

7. The method of claim 1, wherein the reovirus is a recombinant reovirus.

8. The method of claim 1, wherein the reovirus is encapsulated in a micelle.

9. The method of claim 1, wherein the mammal has a solid neoplasm, and the reovirus is administered by injection into or near the solid neoplasm.

10. The method of claim 1, wherein the reovirus is administered into the mammal intravenously, intraperitoneally, intravascularly, subcutaneously, nasally, or by inhalation.

11. The method of claim 1, wherein the mammal is immunocompetent.

12. The method of claim 1, wherein the reovirus is administered in a single dose.

13. The method of claim 1, wherein the reovirus is administered in more than one dose.

14. The method of claim 1, further comprising a step selected from the group consisting of: administering to the mammal an effective amount of an immune suppressive agent; removing anti reovirus antibodies from said mammal; and administering anti-antireovirus antibodies to said mammal.

* * * * *

UNITED STATES PATENT AND TRADEMARK OFFICE
CERTIFICATE OF CORRECTION

| | | |
|---|---|---|
| PATENT NO. | : 7,763,252 B2 | Page 1 of 1 |
| APPLICATION NO. | : 11/807908 | |
| DATED | : July 27, 2010 | |
| INVENTOR(S) | : Matthew C. Coffey | |

It is certified that error appears in the above-identified patent and that said Letters Patent is hereby corrected as shown below:

Title Page, Item [56] References Cited, Other Publications, Carter reference, please delete "anitbody" and insert --antibody-- therefor;

Title Page, References Cited, Other Publications, Chaubert reference, please delete "114(4):767-775" and insert --144(4):767-775-- therefor;

Title Page, References Cited, Other Publications, Cuff reference, please delete "sutdy" and insert --study-- therefor;

Column 21, line 27 (Claim 4), after "reovirus" please insert --.--.

Signed and Sealed this

Seventh Day of December, 2010

David J. Kappos
*Director of the United States Patent and Trademark Office*